(12) United States Patent
Jeyanandarajan (10) Patent No.: US 11,963,783 B2
(45) Date of Patent: Apr. 23, 2024

(54) SYSTEMS AND METHODS FOR BRAIN WAVE DATA ACQUISITION AND VISUALIZATION

(71) Applicant: Dhiraj Jeyanandarajan, Irvine, CA (US)

(72) Inventor: Dhiraj Jeyanandarajan, Irvine, CA (US)

( * ) Notice: Subject to any disclaimer, the term of this patent is extended or adjusted under 35 U.S.C. 154(b) by 266 days.

(21) Appl. No.: 17/411,676

(22) Filed: Aug. 25, 2021

(65) Prior Publication Data

US 2022/0061735 A1 Mar. 3, 2022

Related U.S. Application Data

(60) Provisional application No. 63/070,614, filed on Aug. 26, 2020.

(51) Int. Cl.
*A61B 5/00* (2006.01)
*A61B 5/374* (2021.01)
(Continued)

(52) U.S. Cl.
CPC .............. *A61B 5/374* (2021.01); *A61B 5/384* (2021.01); *G06F 3/015* (2013.01); *G06F 17/142* (2013.01); *G06T 17/20* (2013.01)

(58) Field of Classification Search
None
See application file for complete search history.

(56) References Cited

U.S. PATENT DOCUMENTS

D363,482 S 10/1995 Robinson
D415,146 S 10/1999 Hori
(Continued)

FOREIGN PATENT DOCUMENTS

CN 110058691 A 7/2019
KR 20140128042 A 11/2014
(Continued)

OTHER PUBLICATIONS

Brunet et al. Spatiotemporal Analysis of Multichannel EEG: CARTOOL. Computational Intelligence and Neuroscience. vol. 2011, Article ID 813870, 15 pages. (Year: 2011).*
(Continued)

*Primary Examiner* — Etsub D Berhanu
(74) *Attorney, Agent, or Firm* — Sheppard Mullin Richter & Hampton LLP (57) ABSTRACT

Systems and methods for providing a computer-generated visualization of EEG data are disclosed. Raw EEG data generated from a multi-channel EEG headset (or other device) may be received. The EEG data may be run through a fast Fourier transform (FFT) to separate out various frequency components in each channel, isolating the brain wave components for each channel. A visual display may be generated based on the isolated components comprising a first display portion and a second display portion. The first display portion may comprise a geometrical mesh with predefined parameters representing the portions of a crystal. The second display portion may comprise a time-varying color visualization based on the variance of the brain waves. A composite computer display in which the first display portion is overlaid over the second display portion may be generated and provided via a display device.

18 Claims, 6 Drawing Sheets

(51) Int. Cl.
*A61B 5/384* (2021.01)
*G06F 3/01* (2006.01)
*G06F 17/14* (2006.01)
*G06T 17/20* (2006.01)

(56) References Cited

U.S. PATENT DOCUMENTS

| | | | |
|---|---|---|---|
| 5,978,648 | A | 11/1999 | George |
| D427,982 | S | 7/2000 | Ishii |
| D582,547 | S | 12/2008 | Ungar |
| D688,788 | S | 8/2013 | Spruell |
| D754,864 | S | 4/2016 | Heath |
| D761,257 | S | 7/2016 | Passmore |
| D777,335 | S | 1/2017 | Rurling |
| D781,289 | S | 3/2017 | Patel |
| D791,126 | S | 7/2017 | Sullivan |
| D813,233 | S | 3/2018 | Lee |
| 9,907,482 | B2 | 3/2018 | Knight |
| 10,448,883 | B2 | 10/2019 | Grossman |
| 10,688,274 | B1 | 6/2020 | Jovanov |
| D907,220 | S | 1/2021 | Brown |
| D911,542 | S | 2/2021 | Zhang |
| D916,087 | S | 4/2021 | Wei |
| D918,904 | S | 5/2021 | Jackson |
| D926,336 | S | 7/2021 | Zhang |
| D972,735 | S | 12/2022 | Keller |
| D975,089 | S | 1/2023 | Su |
| D976,901 | S | 1/2023 | Huajun |
| D985,136 | S | 5/2023 | Ma |
| D986,538 | S | 5/2023 | Ling |
| D994,130 | S | 8/2023 | Yi |
| D994,135 | S | 8/2023 | Yu |
| 2003/0207237 | A1 | 11/2003 | Glezerman |
| 2005/0080592 | A1 | 4/2005 | Buscema |
| 2008/0275358 | A1 | 11/2008 | Freer |
| 2009/0062660 | A1 | 3/2009 | Chance |
| 2009/0221928 | A1 | 9/2009 | Einav |
| 2009/0265649 | A1 | 10/2009 | Schlossberg |
| 2009/0319459 | A1 | 12/2009 | Breazeal |
| 2010/0004977 | A1 | 1/2010 | Marci |
| 2010/0042011 | A1* | 2/2010 | Doidge ............ G06T 17/10 600/544 |
| 2010/0274835 | A1 | 10/2010 | Brown |
| 2011/0091847 | A1 | 4/2011 | Carroll |
| 2011/0105859 | A1 | 5/2011 | Popovic |
| 2012/0040326 | A1 | 2/2012 | Larson-Rutter |
| 2013/0177883 | A1 | 7/2013 | Barnehama |
| 2013/0179087 | A1 | 7/2013 | Garripoli |
| 2017/0311831 | A1 | 11/2017 | Freer |
| 2018/0078164 | A1 | 3/2018 | Menon |
| 2019/0000338 | A1 | 1/2019 | Van Den Ende |
| 2019/0200925 | A1 | 7/2019 | Aimone |
| 2020/0060566 | A1 | 2/2020 | Howard |
| 2020/0187857 | A1 | 6/2020 | Jovanovic |
| 2023/0157635 | A1 | 5/2023 | Dhiraj |

FOREIGN PATENT DOCUMENTS

| | | |
|---|---|---|
| WO | 2011057306 | 5/2011 |
| WO | 2014107795 | 7/2014 |
| WO | 2020002519 A1 | 1/2020 |
| WO | 2020250160 A1 | 12/2020 |
| WO | 2021108922 | 6/2021 |

OTHER PUBLICATIONS

Mullen et al. Real-Time Modeling and 3D Visualization of Source Dynamics and Connectivity Using Wearable EEG. 35th Annual International Conference of the IEEE EMBS, Osaka, Japan, Jul. 3-7, 2013. (Year: 2013).*

Thorpe et al. Spectral and source structural development of mu and alpha rhythms from infancy through adulthood. Clinical Neurophysiology, 127 (2016) 254-269. (Year: 2016).*

Harrison, William A., et al., "A New Application of Adaptive Noise Cancellation," IEEE Transactions on Acoustics, Speech, and Signal Processing, vol. AASP-34, No. 1, Feb. 1986, pp. 21-27, doi: 10.1109/TASSP.1986.1164777.

Lee, Boon-Giin, et al., "Smartwatch-Based Driver Alertness Monitoring with Wearable Motion and Physiological Sensor", 2015 37th Annual International Conference of the IEEE Engineering in Medicine and Biology Society (EMBC), vol. 1, Aug. 2015, pp. 6126-6129, doi: 10.1109/EMBC.2015.7319790.

Yang, Dong, et al., "A Novel Adaptive Spectrum Noise Cancellation Approach for Enhancing Heartbeat Rate Monitoring in a Wearable Device", IEEE Access, vol. 6, 2018 (Year: 2018), pp. 8364-8375.

Heraz, Alicia, et al., "Predicting the Three Major Dimensions of the Learner's Emotions from Brainwaves", World Academy of Science, Engineering and Technology International Journal of Computer and Information Engineering, vol. 1, No. 7, 2007, pp. 1994-2000.

Petrantonakis, Panagiotis C., et al., "Emotion Recognition from Brain Signals Using Hybrid Adaptive Filtering and Higher Order Crossings Analysis", IEEE Transactions on Affective Computing, vol. 1, No. 2, Jul.-Dec. 2010, 17 pages.

Yuen, Chai Tong, et al., "Classification of Human Emotions from EEG Signals using Statistical Features and Neural Network", International Journal of Integrated Engineering (Issue on Electrical and Electronic Engineering), 2010, 6 pages.

Discover Your Brain's Potential with Neuphony: Brain Wearable EEG Device & App, Online, published date Sep. 23, 2023, Retrieved on Oct. 27, 2023 from <URL: https://www.youtube.com/watch?v=3sVTQzShc8Q>, 1 page.

Great Britain Application No. 4042004, filed Aug. 12, 2015, in the name of Sean Barry Webber, 2 pages.

* cited by examiner

SYSTEMS AND METHODS FOR BRAIN WAVE DATA ACQUISITION AND VISUALIZATION

CROSS-REFERENCE TO RELATED APPLICATIONS

This application claims priority to U.S. Provisional Patent Application Ser. No. 63/070,614, filed Aug. 26, 2020, entitled "SYSTEMS AND METHODS FOR BRAIN WAVE DATA ACQUISITION AND VISUALIZATION", which is hereby incorporated by reference in its entirety.

FIELD OF THE INVENTION

The present invention relates generally to the detection, decomposition, and display of brain activity.

BACKGROUND OF THE INVENTION

Brain waves can be detected via electroencephalography (EEG), which involves monitoring and recording electrical impulse activity of the brain, typically noninvasively. EEG data can be generated by placing a number of electrodes (often part of a brain-computer interface (BCI) headset) on or near the subject's scalp. The electrodes detect the electrical impulses generated by the brain and send signals to a computer that records the results. The data from each electrode may be deemed a channel representing data from a portion of the brain where the electrode is located. Each channel may have a reference electrode in a montage used in the differential amplification of the source signal.

Brain waves may be detected as a time-varying signal and comprise components having different spectral characteristics such as frequency and power. As an example, brain waves may include the following brain wave components: delta waves, theta waves, alpha waves, beta waves, and gamma waves. The spectral characteristics of the brain waves may indicate different mental states based on factors such as source location, duration, coherence and dominance or amplitude.

SUMMARY OF THE INVENTION

Various embodiments of the present disclosure may include systems and methods for providing a computer-generated representation of EEG data.

EEG data has been used primarily for medical or research purposes but limited applications are there for its use in as an artistic or creative representation of individual or collective brain states.

Synchronicity or coherence of spectral characteristics may be observed between individuals or groups when exposed to similar stimuli. Spectral characteristics may be combined to form group averages of specific characteristics to give a collective summary of the brainwaves of more than one individual.

Computer processing allows the analysis of spectral characteristics into its component parts that may be compared to a set of predefined translation parameters to convert the spectral information in components or attributes of a two- or three-dimensional object or objects, with or without audio and tactile components that may also store information. These objects may be displayed on a digital display, captured to still images, or printed on a two- or three-dimensional medium, or the like Information can be stored, inferred or retrieved from an end digital display, a two- or three-dimensional print of the translated EEG data, or the like.

According to one aspect of the invention, the system may be configured to receive raw EEG data generated from a single multi-channel EEG headset (or other device) connected to an individual. Alternatively the system may be configured to receive raw EEG data generated from multiple multi-channel EEG headsets (or other devices) that are connected to multiple individuals. An isolation component may be configured to run the EEG data through various levels of signal processing to isolate components from the spectral characteristics of the EEG signal. By way of example the raw EEG from each channel may be run through a fast Fourier transform (FFT) to separate out various frequency components in each channel, isolating the brain wave components (e.g., alpha, beta, theta, delta, gamma components) for each channel for pattern classification. In some implementations, the EEG data may be run through a high and low bandpass filter prior to the filtered data being run through the FFT to isolate the spectral frequencies of each channel.

A visualization component may be configured to generate a visual display based on the isolated components. An auditory component may be configured to generate an sonic representation based on the isolated components. A tactile component may be configured to generate a tactile sensory component based on the isolated components. The different components may be combined for example in an animated digital visual/auditory display, a 3D printed material, through the configuration of a 3D pressed crystal, or the like. The isolated spectral characteristics of the signal may be compared to a set of predefined translation parameters that may take the signal processing outputs and translate them into their corresponding output components. The output components may comprise the visual, auditory, tactile outputs of the system. By way of example, isolated spectral characteristics such as the alpha power in the posterior channels may translate to the color blue, while the amplitude in microvolts may translate to a certain dimension of a crystal such as a diamond shapes table size or star length.

In various implementations, the visualization component may be configured to generate a visual display based on the isolated components in which the isolated components are depicted as a two- or three-dimensional shape that may or may not be combined in various forms to generate new shapes or landscapes. For example, the visualization (or visual display) generated based on the isolated components may comprise a diamond or crystal-like shape or any other two- or three-dimensional shape with or without associated auditory components and with or without associated tactile characteristics when transformed into a three-dimensional model. In various implementations, the visual display may comprise a first display portion and a second display portion. In an example implementation, the visualization component may be configured to generate a visual display based on the isolated components in which the isolated components are depicted as a three-dimensional crystal-like shape. The first display portion may comprise a geometrical mesh with predefined parameters representing the portions of a shape (e.g., a crystal-like shape). The visualization component may be configured to generate portions of the shape based on the characteristics of the isolated components. The second display portion may comprise a time-varying color visualization based on the variance of the brain waves. The visualization component may be configured to generate a composite computer display that combines the first display portion with the second display portion.

In various implementations, a processing component may selectively consider two or more of the isolated components of the separated brain waves from each channel and/or region based on, for example, location of source/destination, frequency, timing, and/or mental state. For example, the processing component may utilize ratios and/or other statistical methods to simultaneously consider multiple isolated components. Certain internal physical sources of brain waves may be associated with a specific action or thought process so that considering multiple components (e.g. alpha and gamma) from that source produces a clearer signal representing the thought process being performed. Certain brain wave components may also indicate mood or mental states. Thus, brain wave components from several sources may be simultaneously considered or evaluated (e.g., by determining ratios between separate components).

Group dynamics combining the large scale dynamics of brain wave components across two or more individuals may be simultaneously considered. By way of example, at a music event a group of individuals may be wearing EEG headsets. The system may take the collective input from multiple sources and combine the information to output a single display that can be viewed by the participants.

Once isolated, the visualizer may display the brain waves (or brain wave components) as a multi-faceted three-dimensional shape, such as a three-dimensional crystal shape (e.g., in a traditional diamond cut) with geometric components of the crystal mesh representing various brain waves and/or regions of the brain so that the signals may in turn be retrieved. The mesh sizing and shape may vary over time as the component brain waves change. In some implementations, various colors, arcs, and patterns may be displayed within the crystal mesh to represent the signals considered together from channels, regions, or frequencies of the brain onto the crystal mesh for easy interpretation by viewers. The combination of the isolated brain waves may provide additional metadata and interpretive data to the visualizer. The composite signals based on the ratio between multiple isolated brain waves may also be displayed by the visualizer. In this way, individual brain wave components that warrant highlighting or emphasis based on their representation of specific actions or thoughts may be displayed by the visualizer and not lost in a plethora of other signals.

These and other objects, features, and characteristics of the system and/or method disclosed herein, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

BRIEF DESCRIPTION OF THE DRAWINGS

The drawings are provided for purposes of illustration only and merely depict typical or example implementations. These drawings are provided to facilitate the reader's understanding and shall not be considered limiting of the breadth, scope, or applicability of the disclosure. For clarity and ease of illustration, these drawings are not necessarily drawn to scale.

DETAILED DESCRIPTION OF THE DRAWINGS

The invention described herein relates to systems and methods for providing a computer-generated visualization of EEG data. In various implementations, the system may be configured to receive raw EEG data generated from a multi-channel EEG headset (or other device). An isolation component may be configured to apply various levels of signal processing to isolate components from the spectral characteristics of the EEG signal. By way of example the raw EEG data from each channel may be run through a fast Fourier transform (FFT) to separate out various frequency components in each channel, isolating the brain wave components (e.g., alpha, beta, theta, delta, gamma components) for each channel for pattern classification. A visualization component may be configured to generate a visual display based on the isolated components. In various implementations, the visualization component may be configured to generate a visual display based on the isolated components in which the isolated components are depicted as a two- or three-dimensional shape and/or a fractal landscape consisting of a series of repeating shapes. For example, the visualization (or visual display) generated based on the isolated components may comprise a diamond or crystal-like shape or any other two- or three-dimensional shape. In various implementations, the visual display may comprise a first display portion and a second display portion. In an example implementation, the visualization component may be configured to generate a visual display based on the isolated components in which the isolated components are depicted as a three-dimensional crystal-like shape. The first display portion may comprise a geometrical mesh with predefined parameters representing the portions of a shape (e.g., a crystal-like shape). The visualization component may be configured to generate portions of the shape based on the characteristics of the isolated components. The second display portion may comprise a time-varying color visualization based on the variance of the brain waves. The visualization component may be configured to generate a composite computer display that combines the first display portion over the second display portion.

It will be appreciated by those having skill in the art that the implementations described herein may be practiced without these specific details or with an equivalent arrangement. In various instances, well-known structures and devices are shown in block diagram form to avoid unnecessarily obscuring the implementations.

Example System Architecture

Figure 1:
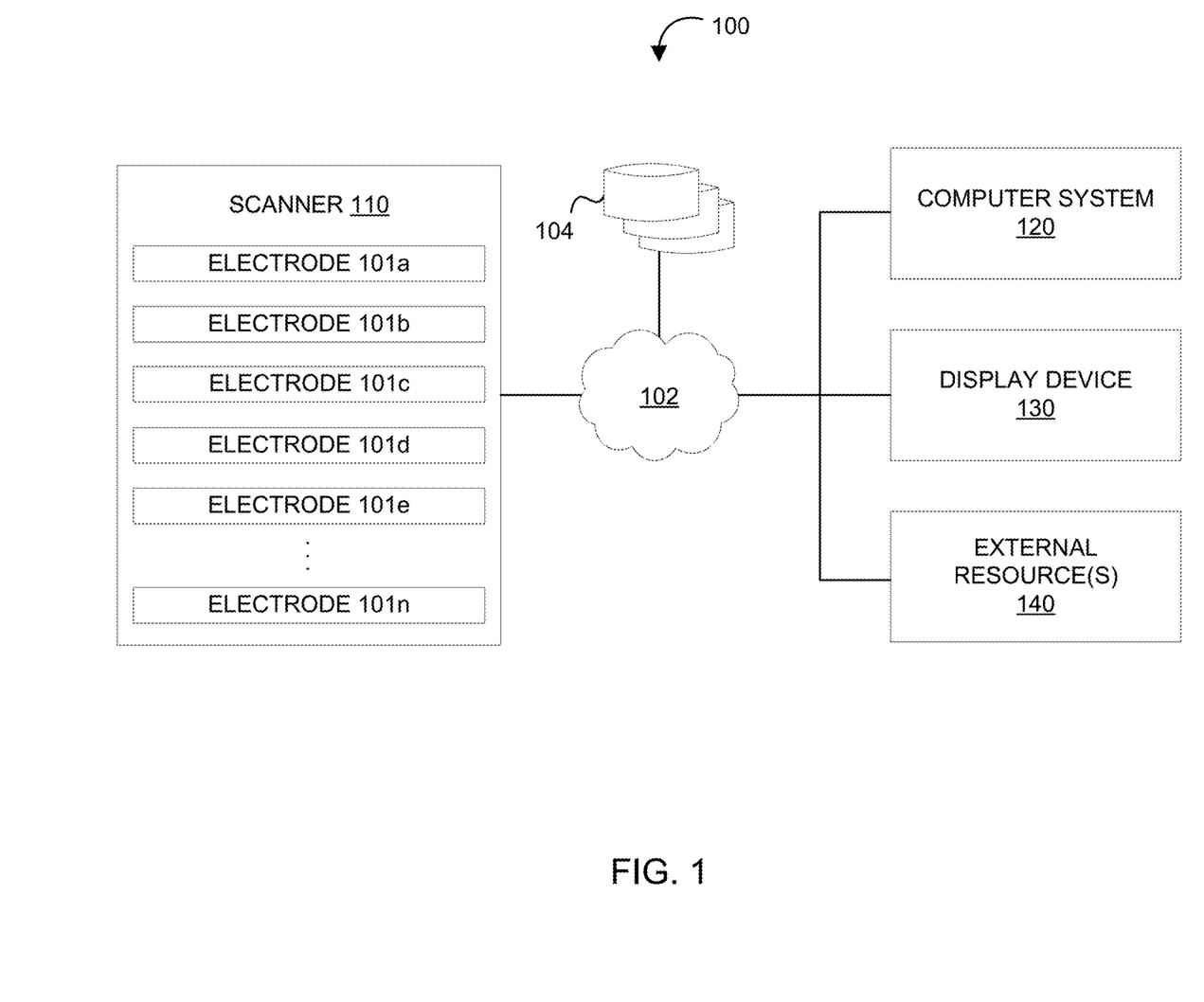
FIG. 1 illustrates a block diagram of an example of a system for scanning, detecting, and displaying synthesized brain waves, in accordance with one or more implementations of the invention.

FIG. 1 depicts a block diagram of an example of a system 100 for scanning, detecting, and displaying synthesized brain waves, in accordance with one or more implementations of the invention. In various implementations, system 100 may include one or more storage devices 104, a scanner 110, a computer system 120, a display device 130, one or more external resources 140, and/or other components. In various implementations, scanner 110 may comprise a head-mounted device and/or other device. In various implementations, scanner 110 may comprise an electroencephalography (EEG) device configured to sense the electrical activity inside a person's brain. For example, scanner 110 may comprise a device on or near scalp of a patient at multiple points via electrodes 101 or connects directly to the brain or skull via inserted probes as in electrocorticography (ECoG), intracranial electroencephalography (iEEG), or subdural EEG (SD-EEG). In various implementation, scanner 110 may comprise a multi-channel EEG headset.

In various implementations, scanner 110 may include a set of electrodes 101 (e.g., electrode 101a, electrode 101b, electrode 101c, electrode 101d, electrode 101e, . . . , and/or electrode 101n). Scanner 100 may comprise anywhere from a low density (e.g., 2-channel system) to a high density (e.g., 256-channel system) array of electrodes. In various implementations, each electrode 101 may be attached to a patient's head (or scalp) and configured to receive brain waves. For example, scanner 110 may comprise a 4-channel EEG system with a ground and reference. In some implementations, each electrode 101 may correspond to a specific channel input of the scanner. For example, an electrode 101a may correspond to a channel 101a, an electrode 101b may correspond to a channel 101b, etc. In some embodiments, each channel may have a reference electrode in a montage used in the differential amplification of the source signal The channels of each electrode may be configured to receive different components, for example such as delta, theta, alpha, beta, and/or gamma signals—each of which may correspond to a given frequency range. In a non-limiting example implementation, delta waves may correspond to signals between 0 and 3.5 Hz, theta waves may correspond to signals between 3.5 and 8 Hz, alpha waves may correspond to signals between 8 and 12 Hz, beta waves may correspond to signals between 12 and 30 Hz, and gamma waves may correspond to signals above 30 Hz. These example frequency ranges are not intended to be limiting and are to be considered exemplary only.

In some implementations, the electrodes 101 may be attached at locations spread out across the patient's head (or scalp) and/or centered over each of the primary regions of the brain. Electrodes 101 may be configured to detect electric potentials generated by the brain from the low ionic current given off by the firing of synapses and neural impulses traveling within neurons in the brain. These electric potentials may repeat or be synchronized at different spectral characteristics such as frequency and power according to the previously listed brain wave types (e.g. alpha and beta). These spectral characteristics of the brain waves may be separated from the single superimposed frequency signal detected at each electrode by scanner 110 or computer system 120 as described further herein. In various implementations, this isolation, separation, decomposition, or deconstruction of the signal is performed via application of a fast Fourier transform (FFT).

In various implementations, computer system 120 may be configured to receive raw EEG data generated by scanner 110. In some implementations, scanner 110 and/or computer system 120 may be configured to perform initial signal processing on the detected brain waves. For example, scanner 110 and/or computer system 120 may be configured to run the raw EEG data through a high and low bandpass filter prior to the filtered data being run through a FFT to isolate the spectral frequencies of each channel. For example, each channel may be run through a high and low bandpass filter. In some implementations, scanner 110 and/or computer system 120 may be configured to perform error detection, correction, signal decomposition, signal recombination, and other signal analysis. Accordingly, one or both of scanner 110 and computer system 120 may be configured to filter, analyze, and/or otherwise process the signals captured by scanner 110.

In an example implementation using the 10-20 international system of electrode placement, Channel 1 may correspond to the Fp1 location, Channel 2 may correspond to Fp2, Channel 3 may correspond to T5, and Channel 4 may correspond to T6. The ground and reference electrodes may be placed on either side of the earlobe. As described herein, filtered data for each channel may be run through a fast Fourier transform (FFT) to isolate the spectral frequencies of each channel. The power of the theta (e.g., 4-7 Hz), alpha (e.g., 8-12 Hz), beta (e.g., 13-20 Hz), and gamma (e.g., 21-50 Hz) components of each channel for a given sampled timeframe (e.g., 3 seconds) may be determined. The power of each of the isolated components may be used to generate a visualization of the brain wave components, as described herein. For example, to generate a model for a visual display comprising a crystal or diamond-like shape, theta power from Channels 1 & 2 (min to max) may be used as inputs for crown height and table (respectively) of the diamond model, theta power from Channels 1 & 2 (min to max) may be used as inputs for size and color of the particle elements (respectively) of the circle waveform in the spectral visualizer, alpha power from Channels 3 & 4 (min to max) may be used as inputs for the diameter and pavilion depth (respectively) of the diamond model, and alpha power from Channels 3 & 4 (min to max) may be used as inputs for the color and rotation speed (respectively) of the sphere waveform in the spectral visualizer. Various additional and/or alternative combinations of the isolated components may be utilized to fine tune the aesthetic appearance of the visualization. As described herein, the foregoing isolated components, when combined with additional isolated components from the same or a different channel, may be used to generate a real-time visualization of brain wave activity within a diamond (or crystal) that changes in real-time in accordance with the EEG data obtained by scanner 110.

One or more other visualizations may be generated using the techniques described herein. For example, in some implementations, system 100 may utilize the various components and techniques described herein to generate a real-time visualization of brain wave activity that is overlaid onto an image or video captured and/or obtained by system 100. For example, in some implementations, system 100 may include an image capture device. System 100 may be configured to capture an image or video via image capture device and/or otherwise obtain an image or video. In various implementations, system 100 may be configured to apply an object recognition algorithm to the image or video to identify one or more objects within the image or video. For example, the object recognition algorithm may be configured to identify a person within the image or video. In various implementations, the image or video may be captured and/or obtained in real-time while EEG data for an individual is simultaneously being captured. For example, the EEG data may be captured for an individual while an image or video of that individual is simultaneously being captured. In various implementations, system 100 may be configured to translate the EEG data into audio and/or visual outputs. For example, system 100 may be configured to translate the EEG data into audio and/or visual outputs using one or more techniques described herein. In some implementations, the audio and/or visual outputs may comprise visual effects, such as particle effects similar to a music visualizer which generates animated imagery based on the piece of music being played or performed. In the same vein, the audio and/or visual effects generated by system 100 may comprise animated imagery based on the EEG data being captured. System 100 may be configured to combine the audio and/or visual effects onto the image or video in real-time and/or as recorded to enable later playback. The visual or audiovisual display generated (i.e., the image or video with the audio and/or visual effects generated based on EEG data overlaid onto it) may be presented to a user. In an example implementation in which the image or video is of the user and the visual or audiovisual display comprises visual effects generated based on their EEG data overlaid onto that image or video, a user may shape, participate, and/or otherwise interact with a virtual image of their external environment through their brain signals. For example, as they learn to control their mental or brain state (e.g., by becoming more relaxed), the user can visualize it as a form of interactive neurofeedback. Accordingly, the systems, methods, and techniques described herein may be utilized to train users to control their mental or brain state.

In various implementations, computer system 120 may output data to be displayed to a patient, physician, and/or other user via a display device 130 as described further herein. In some implementations, computer system 120 may be connected to one or more cloud servers and/or storage devices configured to store the EEG data and visualizations generated by computer system 120. Accordingly, the visualizations may be retrieved and viewed at a later time. For example, one or more cloud servers and/or associated storage may be implemented as an electronic health records (EHR) database. External resources 140 may include sources of information outside of system 100, external entities participating with system 100, and/or other resources. In various implementations, computer system 120 may be configured to provide processing capability and perform one or more operations as described further herein with respect to FIGS. 2-4.

Figure 2:
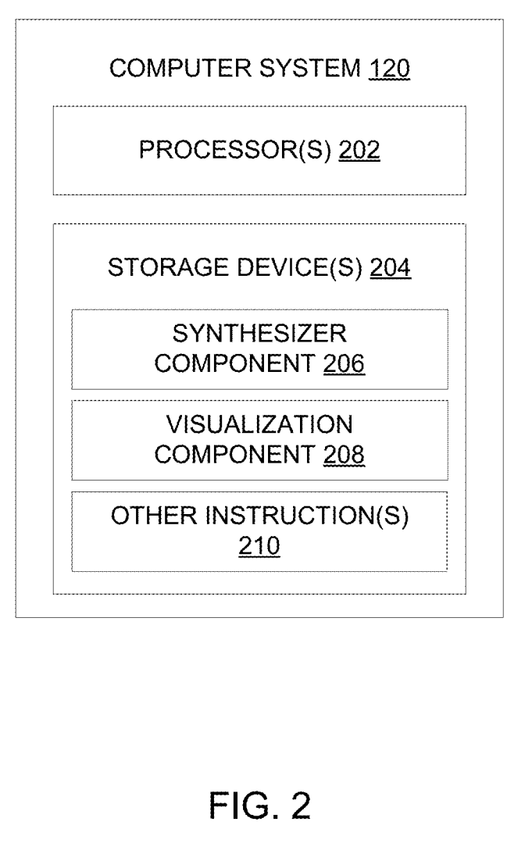
FIG. 2 illustrates a block diagram of an example of a computer system for processing and displaying brain wave signals, in accordance with one or more implementations of the invention.

FIG. 2 depicts a block diagram of an example of a computer system 120 for processing and displaying brain wave signals, in accordance with one or more implementations of the invention. In various implementations, computer system 120 may include one or more processors 202 (also interchangeably referred to herein as processors 202, processor(s) 202, or processor 202 for convenience), one or more storage devices 204, and/or other components. Processor(s) 202 may be configured to provide information processing capabilities in computer system 120. As such, processor(s) 202 may comprise one or more of a digital processor, an analog processor, a digital circuit designed to process information, a central processing unit, a graphics processing unit, a microcontroller, an analog circuit designed to process information, a state machine, and/or other mechanisms for electronically processing information. Operating as a cloud-based system, one or more processors 202 of computer system 120 may be included in a plurality of server platforms and may cooperate to perform the functions that implement and/or instantiate computer system 120. Similarly, one or more storage devices of computer system 120 may be distributed across multiple physical platforms, and cooperate to provide the required storage space. Computer system 120 may therefore operate as a virtualized system.

Processors 202 may be programmed by one or more computer program instructions stored in one or more storage devices 204. For example, processors 202 may be programmed by synthesizer component 206, visualization component 208, and/or other instructions 210 that program computer system 120 to perform various operations, each of which are described in greater detail herein. In various implementations, the instructions that program computer system 120 to perform various operations may be stored on one or more storage devices 204 and/or other storage devices. As used herein, for convenience, the various instructions will be described as performing an operation, when, in fact, the various instructions program the processors 202 (and therefore computer system 120) to perform the operation.

Synthesizer component 206 may be configured to perform signal decomposition or signal deconstruction of raw EEG data received from a scanner (e.g., scanner 110). In other words, synthesizer component 206 may be configured to cause processors 202 to perform one or more processing operations on signals received from scanner 110 that are necessary to isolate the brain wave components. In various implementations, synthesizer component 206 may be configured to run the EEG data through a fast Fourier transform (FFT) to separate out various frequency components in each channel, isolating the brain wave components (e.g., alpha, beta, theta, delta, gamma components) for each channel. In various implementations, synthesizer component 206 may program processors 202 to perform one or more processing operations on signals received from scanner 110 that are necessary to isolate the brain wave components using all or a portion of the components of synthesizer component 206 illustrated in FIG. 3.

Visualization component 208 may be configured to generate a visualization (or visual display) based on isolated brain wave components. In various implementations, the visualization generated by visualization component 208 may comprise a first display portion and a second display portion. The first display portion may comprise a geometrical mesh with predefined parameters representing the portions of a crystal. In various implementations, visualization component 208 may be configured to generate portions of the crystal based on the characteristics of the isolated components. The second display portion may comprise a time-varying color visualization based on the variance of the brain waves. In various implementations, visualization component 208 may be configured to generate a composite computer display that combines the first display portion over the second display portion. In various implementations, visualization component 208 may program processors 202 to generate a visualization (or visual display) based on the isolated components using all or a portion of the components of visualization component 208 illustrated in FIG. 4.

Figure 3:
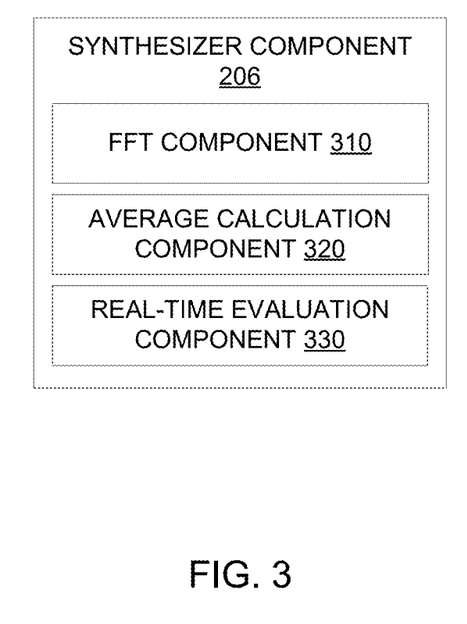
FIG. 3 illustrates a block diagram of an example of a synthesizer component configured to perform signal decomposition or signal deconstruction of raw EEG data received from a scanner, in accordance with one or more implementations of the invention.

FIG. 3 depicts a block diagram of an example of a synthesizer component 206 configured to perform signal decomposition or signal deconstruction of raw EEG data received from a scanner, in accordance with one or more implementations of the invention. In various implementations, synthesizer component 206 may be configured to receive raw EEG data from a scanner (e.g., scanner 110) and perform one or more processing operations on the received raw EEG data. For example, synthesizer component 206 may be configured to perform error correction and cross-correlation of the many channels received. In various implementations, synthesizer component 206 may include one or more components configured to each perform at least one processing operation on the received raw EEG data. For example, synthesizer component may include a fast Fourier transform (FFT) component 310, an average calculation component 320, a real-time evaluation component 330, and/or other components.

FFT component 310 may be configured to run the EEG data through a fast Fourier transform (FFT) to separate out various frequency components in each channel, isolating the brain wave components (e.g., alpha, beta, theta, delta, gamma components) for each channel. The Fourier transform algorithm utilized by FFT component 310 may comprise any discrete Fourier transform technique. In various implementations, FFT component 310 may be configured to, utilizing a FFT, deconstruct a time domain representation of a signal into the frequency domain representation. This deconstruction allows specific frequencies to appear as impulse functions in the frequency domain, allowing those signals to then be isolated. Accordingly, FFT component 310 may also be referred to herein as an "isolation component."

Average calculation component 320 may be configured to compute average activity metrics for brain wave categories (e.g., alpha or delta) and sources (e.g., occipital region) over a given time period (e.g., a previous period of hours, minutes, or seconds). In various implementations, average calculation component 320 may be configured to determine an average or median that can be used to determine which brain wave categories or sources are dominating and which are breaking out more recently via variance from those averages or medians. In some implementations, average calculation component 320 may be compute the long-term average brain wave activity. Accordingly, average calculation component 320 may also be referred to herein as a "long-term average calculation component."

Real-time evaluation component 330 may be configured to analyze the isolated frequency signals from individual channels and add contextual information based on the source of the brain waves, the timing between channels, duration of each category, and amplitude of each category/source. The contextual information may be derived from comparison of the channels via ratios or other statistical methods and use of the averages or stimulus-specific data expectations. For example, certain activities, such as watching a scary movie, may represent stimuli that prompt specific brain wave activity. In various implementations, real-time evaluation component 330 may be configured to analyze whether signals received—from one or more channels—correspond with a particular mental state. In some implementations, real-time evaluation component 330 may be configured to utilize ratios between isolated brain wave components to determine whether the signals received correspond with a particular mental state. For example, cognitive load is a ratio between the alpha and theta components of the occipital and temporal channels.

Over-arousal in certain brain areas may be linked with anxiety disorders, sleep problems, nightmares, hyper-vigilance, impulsive behavior, anger/aggression, agitated depression, chronic nerve pain, and spasticity. Under-arousal in certain brain areas may correlate with some types of depression, attention deficit, chronic pain, and insomnia. A combination of regional under-arousal and over-arousal may be seen in cases of anxiety, depression, and ADHD. Instabilities in brain rhythms correlate with tics, obsessive-compulsive disorder, panic attacks, bipolar disorder, narcolepsy, epilepsy, sleep apnea, vertigo, tinnitus, anorexia/bulimia, PMT, diabetes, hypoglycemia, and explosive behavior. These disorders or their precursors may be identified by real-time evaluation component 330 and selectively displayed or indicated to a user or medical professional, as described further herein with respect to visualization component 208.

Figure 4:
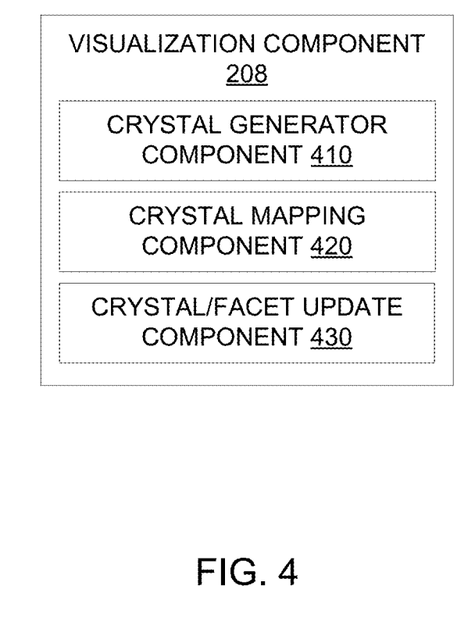
FIG. 4 illustrates a block diagram of an example of a visualization component configured to generate a visualization (or visual display) based on isolated brain wave components, in accordance with one or more implementations of the invention.

FIG. 4 depicts a block diagram of an example of a visualization component 208 configured to generate a visualization (or visual display) based on isolated brain wave components, in accordance with one or more implementations of the invention. In various implementations, visualization component 208 may be configured to generate a visual display based on the isolated components comprising a first display portion and a second display portion. The first display portion may comprise a geometrical mesh with predefined parameters representing the portions of a crystal. In some implementations, visualization component 208 may be configured to generate portions of the crystal based on the characteristics of the isolated components. The second display portion may comprise a time-varying color visualization based on the variance of the brain waves. In some implementations, visualization component 208 may be configured to generate a composite computer display that combines the first display portion with the second display portion. In various implementations, visualization component 208 may be configured to output the generated visualization(s) to a display device 130 for display. In various implementations, visualization component 208 may include one or more components configured to assist in the generation of the visualizations described herein. For example, visualization component 208 may include a crystal generator component 410, a crystal mapping component 420, a crystal/facet update component 430, and/or other components.

Crystal generator component 410 may be configured to generate a geometrical mesh appearing as facets of a crystal to depict brain activity. For example, crystal generator component 410 may be configured to receive information on indicating average brain wave activity from average calculation component 320 and generate a geometrical mesh that depicts brain wave activity over a time period as a crystal. The geometrical mesh representing the portions of a crystal may comprise the first display portion described herein. In various implementations, the facets of the crystal may be pre-assigned to brain wave categories (e.g. alpha or delta) or sources (e.g. parietal region). Based on the pre-assigned brain wave categories or sources, crystal generator component 410 may be configured to generate a geometrical mesh that is sized based on the recent brain wave activity as evaluated by synthesizer component 206. In some implementations, facets of the crystal may be pre-assigned and/or dynamically adjusted based on parameters associated with the mapping of brain wave categories or sources to facets of the crystal. For example, a user may provide user input to modify parameters that indicate associations between crystal shape, size, and/or orientation and the individual brain wave categories or sources.

Crystal mapping component 420 may be configured to generate a time-varying color visualization based on the variance of the brain waves. The time-varying color visualization may comprise the second display portion described herein. In various implementations, crystal mapping component 420 may be configured to generate a real-time or near real-time display of synthesized brain waves received from synthesizer component 206. For example, crystal mapping component 420 may be configured to generate a real-time or near real-time display of synthesized brain waves on the crystal facets or faces. In some implementations, crystal mapping component 420 may be configured to generate orbs and/or arcs that extend across one or more crystal facets. For example, the triangular facets of the crystal may be used to display alpha brain waves and may be sized according to average amplitude during a given time period.

Crystal/facet update component 430 may be configured to update the visualization of brain wave signals based on processed information received from synthesizer component 206. For example, crystal/facet update component 430 may be configured to receive an indication of average brain activity and determine when to make adjustments to the crystal facets, shape, outline, orientation, and/or other aspects of the visualization. In some implementations, crystal/facet update component 430 may be configured to update the geometric mesh of the crystal itself based on inputs received from synthesizer component 206 (e.g., average calculation component 320) and/or update the information mapped to the facets based on inputs received from synthesizer component 206 (e.g., real-time evaluation component 330). In some implementations, system 100 may be configured to receive user input identifying parameters associated with the mapping of brain wave categories or sources to facets of the crystal (e.g., via display device 130). For example, a user may provide user input to modify parameters that indicate associations between crystal shape, size, and/or orientation and the individual brain wave categories or sources. Based on the user input received, crystal/facet update component 430 may be configured to update the visualization generated.

Figure 5:
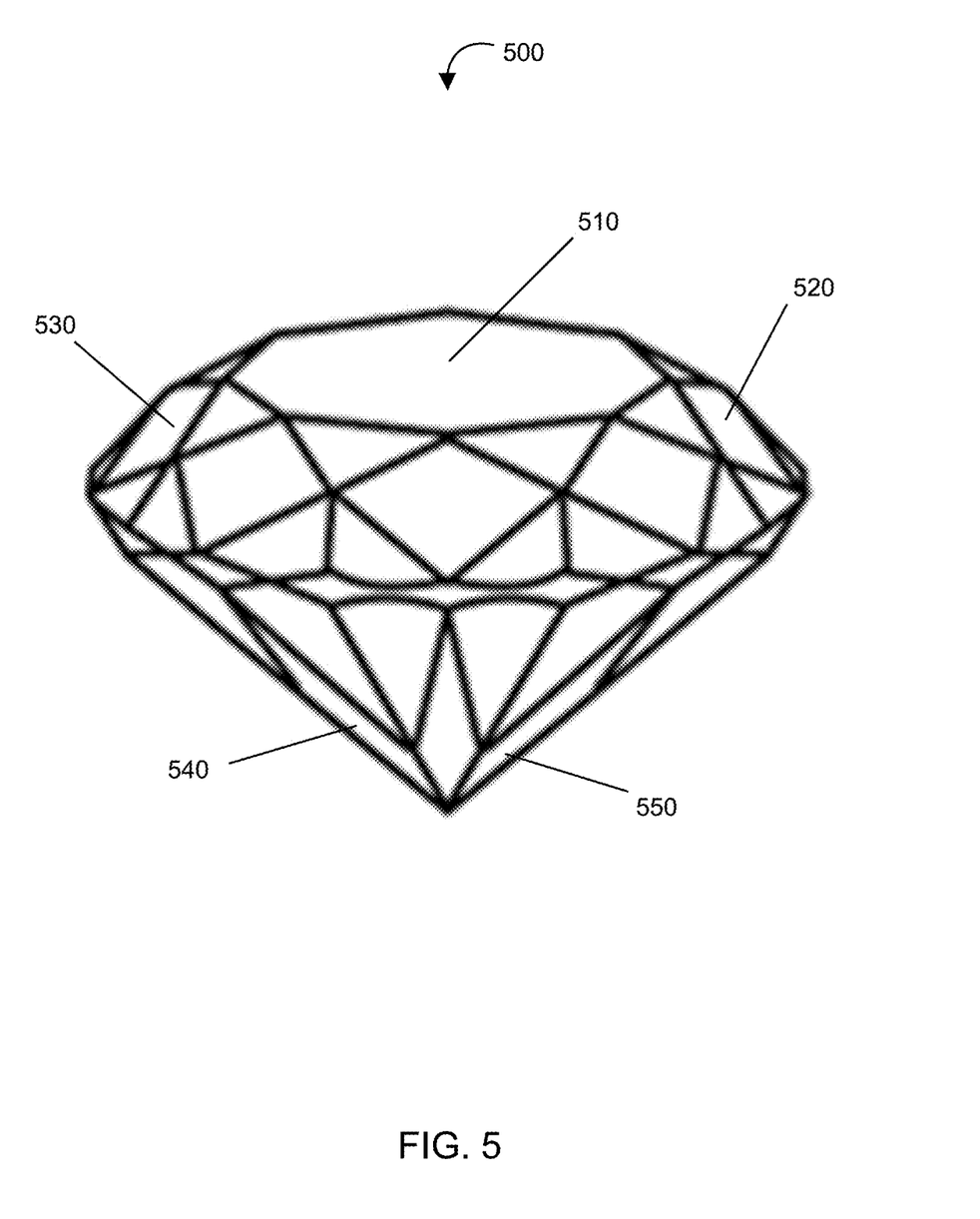
FIG. 5 illustrates an example geometrical mesh or crystal facet arrangement, in accordance with one or more implementations of the invention.

FIG. 5 depicts an example geometrical mesh or crystal facet arrangement 500, in accordance with one or more implementations of the invention. For example, geometrical mesh or crystal facet arrangement 500 may include facets 510, 520, 530, 540, and 550. geometrical mesh or crystal facet arrangement 500 may comprise a first display portion as described herein. First display portion may be based on any crystal shape, including octahedral, hexagonal, triclinic, tetragonal, and/or other artificial polyhedron shapes. In various implementations, the facets may be assigned to specific uses or components of the information to be displayed. For example, the rhomboidal facets 540 and 550 at the base of the crystal may be utilized to display the theta components of different channels of brainwaves such that the flow of theta brain waves may be visualized in a common area.

Example geometrical mesh or crystal facet arrangement 500 may include facets of a crystal to highlight features of recent brain activity to the user or medical practitioner. The facets of the crystal may be pre-assigned to brain wave categories (e.g. alpha or delta) or sources (e.g. parietal region) and then re-sized based on average activity, as described herein. In some implementations, assigned crystal facets may be labeled for visual reference. The shape, size, and orientation of the crystal may be static or dynamic. In various implementations, the shape, size, and orientation of the crystal may be defined by crystal generator component 410, as described herein. In various implementations, the overlay of the brain wave information onto the crystal may be defined by crystal mapping component 420, as described herein.

Figure 6A:
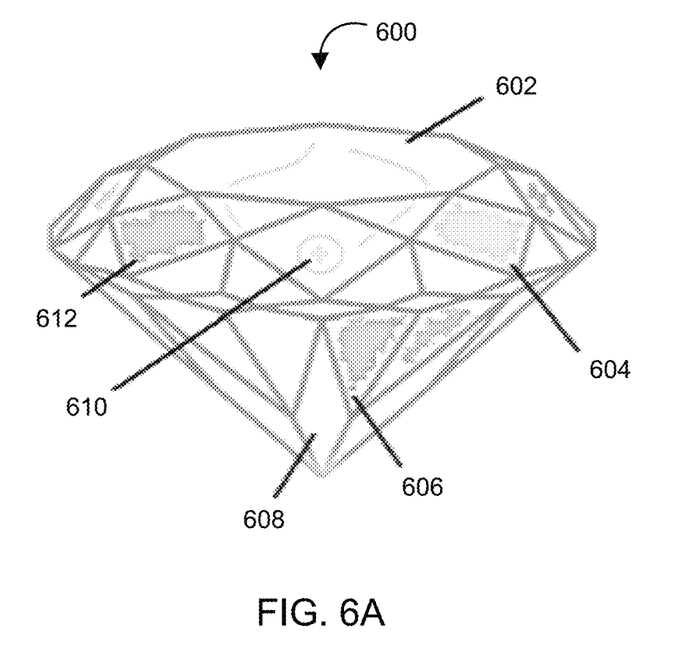
FIG. 6A illustrates an example display of a synthesized brain wave signal mapped to crystal facets, in accordance with one or more implementations of the invention.

FIG. 6A depicts an example display 600 of a synthesized brain wave signal mapped to crystal facets, in accordance with one or more implementations of the invention. Example display 600 may comprise a composite display, in which the second display portion is overlaid the first display portion, as described herein. Example display 600 may include facets 604, 606, 612 and/or other facets displaying various colors and patterns that reflect real-time or near real-time brain wave activity (or recorded brain wave activity), top facet 602 displaying lines of an arc that extends across several facets below top facet 602, and/or other facets that include a visualization of brain wave activity based on isolated brain wave components. In some implementations, arcs may be displayed as being internal to (or within) the crystal along with orb 610. The arcs may illustrate connections between facet information, different parallel thought processes, or estimated transmission vectors within the brain being scanned (e.g., by scanner 110). Because orb 605 and arcs are internal to the crystal, changes in orientation of the crystal, by user rotation, would move orb 605 and arcs so that orb 605 and the arcs are displayed on other facets. In various implementations, the brain wave information may be displayed by a combination of colors, arcs, and/or patterns via a time-varying color visualization based on the variance of the brain waves. In some implementation, the brain wave information (and the corresponding visualization) may be updated in real-time (or near real-time) as the system processes newly received brain signals.

Figure 6B:
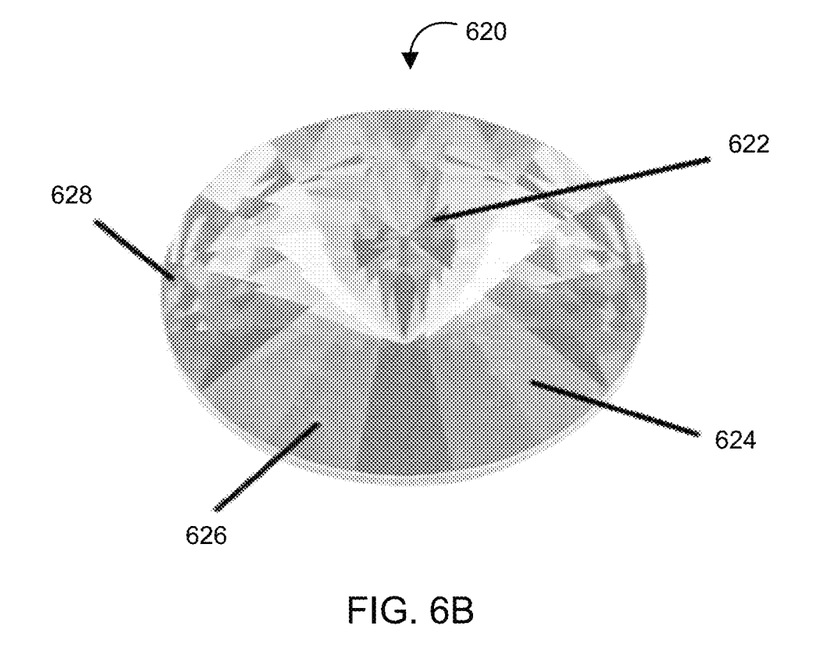
FIG. 6B illustrates an example top-view display of a synthesized brain wave signal mapped to crystal facets, in accordance with one or more implementations of the invention.

FIG. 6B depicts an example top-view display 620 of a synthesized brain wave signal mapped to crystal facets, in accordance with one or more implementations of the invention. In some implementations, example top-view display 620 may comprise a supplementary and/or alternative visualization of the brain wave information to example display 600. Example top-view display 620 may include facets shaded with different colors, including facets 622, 624, 626, and 628. The variations in color may represent different aspects of brain wave information and/or different isolated brain wave components. In an example implementation, a common color or shade may represent a common mental state, bodily action, thought process, or received sensory perception across multiple facets. The facets may then represent various sources of the mental states, bodily actions, thought processes, or received sensory perceptions (e.g. viewed image). In various implementations, facets may be displayed as semitransparent so that facets behind the facing surface facets are visible. The transparency of the facets may be adjusted so that non-facing facets are not visible, but internally-displayed objects such as the orb 605 are visible behind the facets. Facet transparency may be one of the display parameters adjustable by the user in a GUI generated with the crystal shape.

In some implementations, the visual display of the brain wave components may be provided via an augmented reality (AR) or virtual reality (VR) display device. The AR device may be a pair of 3D goggles with right and left displays to provide stereoscopic vision. A camera included in the AR device may provide the outside or environment view to the user via the internal display or the right/left display may be projected on partially-silvered glass so that the user can also view the surrounding environment. In some implementations, the display device can be a fully-virtual reality 3D viewer, a mixed reality 3D viewer, a 2D heads-up display, or an immersive viewing environment.

Referring back to FIG. 2, display device 130 may be connected to and/or in communication with one or more components of system 100 and may be configured to display a graphical user interface (GUI) that displays the visualization(s) generated by visualization component 208. In various implementations, display device 130 may comprise any device capable of rendering visual displays (or visualizations) generated by visualization component 208. For example, display device 130 may comprise a smartphone, a tablet, a computer, a wearable device (e.g., a headset, a visor, glasses, contact lenses, and/or any other wearable device), a monitor, a projector, and/or any other device configured to render visual displays generated by visualization component. In some implementations, display device 130 may comprise a display of computer system 120. For example, display device 130 may comprise a computer monitor or other visual display device such as, for example, an LCD display, a plasma screen display, a cathode ray tube display, or other display device. In some implementations, a user may interact with a GUI presented on display device 130 via one or more graphical user interface components. For example, a user may directly manipulate the crystal (e.g. via arrows), change various parameters of inputs used to generate the visualization, switch between 3D and 2D views of the crystal, and/or otherwise interact or manipulate the visualization generated by visualization component 208. In various implementations, display device 130 may include a touch screen overlaying or integrated into the entire display (or a portion thereof) to allow users to change the orientation of the crystal, zoom in and out, or change facet display parameters, as described herein.

The description of the functionality provided by the different computer-readable instructions described herein is for illustrative purposes, and is not intended to be limiting, as any of instructions may provide more or less functionality than is described. For example, one or more of the instructions may be eliminated, and some or all of its functionality may be provided by other ones of the instructions. As another example, processor(s) 202 may be programmed by one or more additional instructions that may perform some or all of the functionality attributed herein to one of the computer-readable instructions.

Example Flowchart of Processes

Figure 7:
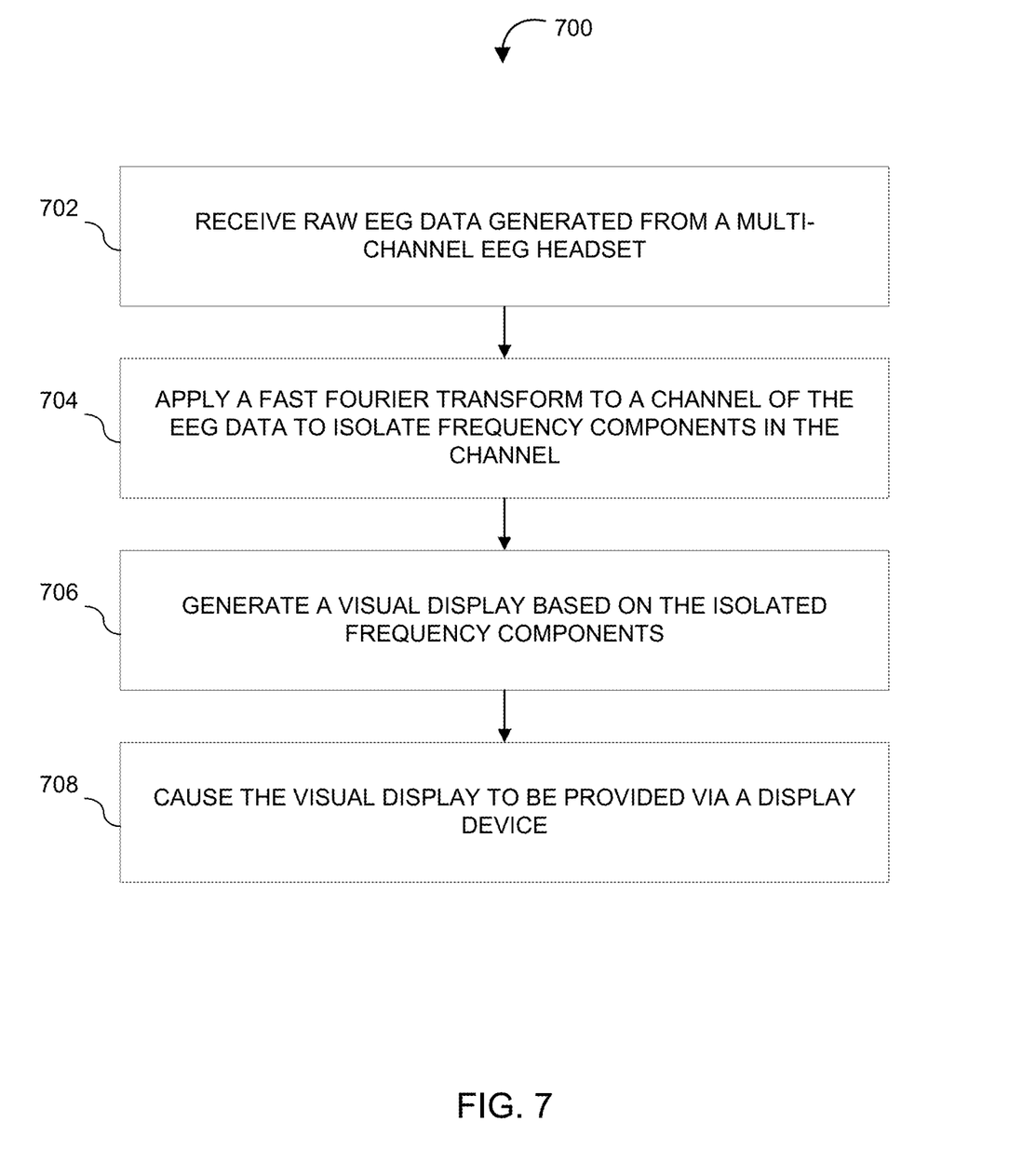
FIG. 7 illustrates an example of a process for providing a computer-generated visualization of EEG data, in accordance with one or more implementations of the invention.

FIG. 7 illustrates an example of a process 700 for providing a computer-generated visualization of EEG data, in accordance with one or more implementations of the invention. The operations of process 700 presented below are intended to be illustrative and, as such, should not be viewed as limiting. In some implementations, process 700 may be accomplished with one or more additional operations not described, and/or without one or more of the operations discussed. In some implementations, two or more of the operations may occur substantially simultaneously. The described operations may be accomplished using some or all of the system components described in detail above.

In some implementations, process 700 may be implemented in one or more processing devices (e.g., a digital processor, an analog processor, a digital circuit designed to process information, a central processing unit, a graphics processing unit, a microcontroller, an analog circuit designed to process information, a state machine, and/or other mechanisms for electronically processing information). For example, process 700 may be implemented by system 100 as described herein. The one or more processing devices may include one or more devices executing some or all of the operations of process 700 in response to instructions stored electronically on one or more electronic storage mediums. The one or more processing devices may include one or more devices configured through hardware, firmware, and/or software to be specifically designed for execution of one or more of the operations of process 700.

In an operation 702, process 700 may include receiving raw EEG data generated from a multi-channel EEG headset. In some implementations, operation 702 may be performed by one or more processor components the same as or similar to synthesizer component 206 (shown in FIG. 2 and FIG. 3 and described herein).

In an operation 704, process 700 may include applying a fast Fourier transform (FFT) to a channel of the EEG data to isolate frequency components in the channel. For example, the EEG data may be isolated into one or more of the components (e.g., alpha, beta, theta, delta, or gamma components) of the channel. In some implementations, operation 704 may be performed by one or more processor components the same as or similar to synthesizer component 206 (shown in FIG. 2 and FIG. 3 and described herein).

In an operation 706, process 700 may include generating a visual display based on the isolated frequency components. In various implementations, the visual display may comprise a first display portion and a second display portion. The first display portion may comprise a geometrical mesh based on the isolated components with predefined parameters representing the geometrical mesh as facets of a crystal. The second display portion may comprise a time-varying color visualization based on time-varying signals of the isolated components. In various implementations, generating the visual display based on the isolated frequency components may include generating a composite computer display that combines the second display portion with the first display portion. In some implementations, operation 706 may be performed by one or more processor components the same as or similar to visualization component 208 (shown in FIG. 2 and FIG. 4 and described herein).

In an operation 708, process 700 may include causing the visual display to be provided via a display device.

The various processing operations and/or data flows depicted in FIG. 7 (and in the other drawing figures) are described in greater detail herein. The described operations may be accomplished using some or all of the system components described in detail above and, in some implementations, various operations may be performed in different sequences and various operations may be omitted. Additional operations may be performed along with some or all of the operations shown in the depicted flow diagrams. One or more operations may be performed simultaneously. Accordingly, the operations as illustrated (and described in greater detail below) are exemplary by nature and, as such, should not be viewed as limiting.

For purposes of explanation, numerous specific details are set forth in order to provide a thorough understanding of the description. It will be appreciated by those having skill in the art that the implementations described herein may be practiced without these specific details or with an equivalent arrangement. Accordingly, it is to be understood that the technology is not limited to the disclosed implementations, but, on the contrary, is intended to cover modifications and equivalent arrangements that are within the spirit and scope of the appended claims. For example, it is to be understood that the present technology contemplates that, to the extent possible, one or more features of any implementation can be combined with one or more features of any other implementation.

Implementations of the disclosure may be made in hardware, firmware, software, or any suitable combination thereof. Aspects of the disclosure may be implemented as instructions stored on a machine-readable medium, which may be read and executed by one or more processors. A machine-readable medium may include any mechanism for storing or transmitting information in a form readable by a machine (e.g., a computing device). For example, a tangible computer readable storage medium may include read only memory, random access memory, magnetic disk storage media, optical storage media, flash memory devices, and others, and a machine-readable transmission media may include forms of propagated signals, such as carrier waves, infrared signals, digital signals, and others. Firmware, software, routines, or instructions may be described herein in terms of specific exemplary aspects and implementations of the disclosure, and performing certain actions.

The various instructions described herein are exemplary only. Other configurations and numbers of instructions may be used, so long as the processor(s) are programmed to perform the functions described herein. The description of the functionality provided by the different instructions described herein is for illustrative purposes, and is not intended to be limiting, as any of instructions may provide more or less functionality than is described. For example, one or more of the instructions may be eliminated, and some or all of its functionality may be provided by other ones of the instructions.

Although processor(s) 202 is illustrated in FIG. 2 as a single component, this is for illustrative purposes only. In some implementations, processor(s) 202 may comprise multiple processing units. These processing units may be physically located within the same device, or processor(s) 202 may represent processing functionality of multiple devices operating in coordination. In some implementations, one or more processors 202 may be implemented by a cloud of computing platforms operating together as one or more processors 202. Processor(s) 202 be configured to execute one or more components by software; hardware; firmware; some combination of software, hardware, and/or firmware; and/or other mechanisms for configuring processing capabilities on processor(s) 202. As used herein, the term "component" may refer to any component or set of components that perform the functionality attributed to the component. This may include one or more physical processors during execution of processor readable instructions, the processor readable instructions, circuitry, hardware, storage media, or any other components. Furthermore, it should be appreciated that although the various instructions are illustrated in FIGS. 2-4 as being co-located within a single processing unit, in implementations in which processor(s) 202 include multiple processing units, one or more instructions may be executed remotely from the other instructions.

The various instructions described herein may be stored in a storage device, which may comprise random access memory (RAM), read only memory (ROM), and/or other memory. For example, one or more storage devices 104 may comprise any tangible computer readable storage medium, including random access memory, read only memory, magnetic disk storage media, optical storage media, flash memory devices, and/or other memory configured to computer-program instructions. In various implementations, one or more storage device 104 may be configured to store the computer program instructions (e.g., the aforementioned instructions) to be executed by the processors as well as data that may be manipulated by the processors. The storage device may comprise floppy disks, hard disks, optical disks, tapes, or other storage media for storing computer-executable instructions and/or data.

One or more databases may be stored in one or more storage devices 104. The databases described herein may be, include, or interface to, for example, an Oracle™ relational database sold commercially by Oracle Corporation. Other databases, such as Informix™, DB2 (Database 2) or other data storage, including file-based, or query formats, platforms, or resources such as OLAP (On Line Analytical Processing), SQL (Structured Query Language), a SAN (storage area network), Microsoft Access™ or others may also be used, incorporated, or accessed. The database may comprise one or more such databases that reside in one or more physical devices and in one or more physical locations. The database may store a plurality of types of data and/or files and associated data or file descriptions, administrative information, or any other data.

The various components illustrated in FIGS. 1-4 may be coupled to at least one other component via a network 102, which may include any one or more of, for instance, the Internet, an intranet, a PAN (Personal Area Network), a LAN (Local Area Network), a WAN (Wide Area Network), a SAN (Storage Area Network), a MAN (Metropolitan Area Network), a wireless network, a cellular communications network, a Public Switched Telephone Network, and/or other network. In FIG. 1, as well as in other drawing Figures, different numbers of entities than those depicted may be used. Furthermore, according to various implementations, the components described herein may be implemented in hardware and/or software that configure hardware.

In some instances, well-known structures and devices are shown in block diagram form in order to avoid unnecessarily obscuring the description. In other instances, functional block diagrams and flow diagrams are shown to represent data and logic flows. The components of block diagrams and flow diagrams (e.g., modules, blocks, structures, devices, features, etc.) may be variously combined, separated, removed, reordered, and replaced in a manner other than as expressly described and depicted herein.

Reference in this specification to "one implementation", "an implementation", "some implementations", "various implementations", "certain implementations", "other implementations", "one series of implementations", or the like means that a particular feature, design, structure, or characteristic described in connection with the implementation is included in at least one implementation of the disclosure. The appearances of, for example, the phrase "in one implementation" or "in an implementation" in various places in the specification are not necessarily all referring to the same implementation, nor are separate or alternative implementations mutually exclusive of other implementations. Moreover, whether or not there is express reference to an "implementation" or the like, various features are described, which may be variously combined and included in some implementations, but also variously omitted in other implementations. Similarly, various features are described that may be preferences or requirements for some implementations, but not other implementations.

The language used herein has been principally selected for readability and instructional purposes, and it may not have been selected to delineate or circumscribe the inventive subject matter. Other implementations, uses, and advantages of the invention will be apparent to those skilled in the art from consideration of the specification and practice of the invention disclosed herein. The specification should be considered exemplary only, and the scope of the invention is accordingly intended to be limited only by the following claims.

What is claimed is:

1. A system for providing a computer-generated visualization of electroencephalography (EEG) data, the system comprising:
   a hardware processor; and
   a non-transitory machine-readable storage medium encoded with instructions executable by the hardware processor to perform operations comprising:
   receiving, by a computer system, raw EEG data generated from a multi-channel EEG headset;
   isolating, by the computer system, brain wave components in at least one EEG channel of the multi-channel EEG headset;
   generating, by the computer system, a visual display based on the isolated brain wave components, the visual display comprising a first display portion and a second display portion, the first display portion comprising a geometrical mesh based on the isolated brain wave components, the second display portion comprising a time-varying color visualization based on time-varying signals of the isolated brain wave components; and
   generating, by the computer system, a composite computer display that combines the second display portion over the first display portion; and
   wherein the geometrical mesh has a three-dimensional crystal shape having multiple facets and each facet represents a respective one of the isolated brain wave components.

2. The system of claim 1, wherein isolating, by the computer system, brain wave components in the at least one EEG channel comprises:
   applying, by the computer system, a fast Fourier transform to at least one EEG channel of the raw EEG data.

3. The system of claim 1, further comprising instructions executable by the hardware processor to perform the operation of:
   controlling an appearance of each facet according to an aspect of a respective isolated brain wave component.

4. The system of claim 1, wherein the hardware processor is configured to:
   control an appearance of each facet according to an aspect of a respective isolated brain wave component according to a respective parameter; and
   modify the parameters according to user input.

5. The system of claim 1, wherein generating the visual display based on the isolated brain wave components comprises:
   generating, by the computer system, an arc connecting multiple facets, the arc representing a connection between information related to each of the multiple facets.

6. The system of claim 1, wherein the isolated frequency brain wave components comprise at least one of:
   an alpha brain wave component;
   a beta brain wave component;
   a theta brain wave component;
   a delta brain wave component; or
   a gamma brain wave component.

7. A non-transitory machine-readable storage medium encoded with instructions executable by one or more hardware processors of a computing component for providing a computer-generated visualization of electroencephalography (EEG) data, the machine-readable storage medium comprising instructions to cause the one or more hardware processors to perform operations comprising:
   receiving, by a computer system, raw EEG data generated from a multi-channel EEG headset;
   isolating, by the computer system, brain wave components in at least one EEG channel of the multi-channel EEG headset;
   generating, by the computer system, a visual display based on the isolated brain wave components, the visual display comprising a first display portion and a second display portion, the first display portion comprising a geometrical mesh based on the isolated brain wave components, the second display portion comprising a time-varying color visualization based on time-varying signals of the isolated brain wave components; and
   generating, by the computer system, a composite computer display that combines the second display portion over the first display portion; and
   wherein the geometrical mesh has a three-dimensional crystal shape having multiple facets and each facet represents a respective one of the isolated brain wave components.

8. The non-transitory machine-readable storage medium of claim 7, wherein isolating, by the computer system, brain wave components in the at least one EEG channel comprises:
   applying, by the computer system, a fast Fourier transform to at least one EEG channel of the raw EEG data.

9. The non-transitory machine-readable storage medium of claim 7, wherein the operations further comprise:
   controlling an appearance of each facet according to an aspect of a respective isolated brain wave component.

10. The non-transitory machine-readable storage medium of claim 7, wherein the operations further comprise:
    controlling an appearance of each facet according to an aspect of a respective isolated brain wave component according to a respective parameter; and
    modifying the parameters according to user input.

11. The non-transitory machine-readable storage medium of claim 7 wherein generating the visual display based on the isolated brain wave components comprises:
    generating, by the computer system, an arc connecting multiple facets, the arc representing a connection between information related to each of the multiple facets.

12. The non-transitory machine-readable storage medium of claim 7, wherein the isolated brain wave components comprise at least one of:
    an alpha brain wave component;
    a beta brain wave component;
    a theta brain wave component;
    a delta brain wave component; or
    a gamma brain wave component.

13. A computer-implemented method for providing a computer-generated visualization of electroencephalography (EEG) data, the method being implemented on a computer system having one or more physical processors programmed with computer program instructions that, when executed by the one or more physical processors, cause the computer system to perform operations comprising:
    receiving, by the computer system, raw EEG data generated from a multi-channel EEG headset;

isolating, by the computer system, brain wave components in at least one EEG channel of the multi-channel EEG headset;

generating, by the computer system, a visual display based on the isolated brain wave components, the visual display comprising a first display portion and a second display portion, the first display portion comprising a geometrical mesh based on the isolated brain wave components, the second display portion comprising a time-varying color visualization based on time-varying signals of the isolated brain wave components; and generating, by the computer system, a composite computer display that combines the second display portion over the first display portion; and wherein the geometrical mesh has a three-dimensional crystal shape having multiple facets and each facet represents a respective one of the isolated brain wave components.

14. The computer-implemented method of claim 13, wherein isolating, by the computer system, brain wave components in at least one EEG channel comprises:

applying, by the computer system, a fast Fourier transform to at least one EEG channel of the raw EEG data.

15. The computer-implemented method of claim 13, further comprising:

controlling an appearance of each facet according to an aspect of a respective isolated brain wave component.

16. The computer-implemented method of claim 13, wherein the operations further comprise:

controlling an appearance of each facet according to an aspect of a respective isolated brain wave component wave components according to a respective parameter; and modifying the parameters according to user input.

17. The computer-implemented method of claim 13, wherein generating the visual display based on the isolated brain wave components comprises:

generating, by the computer system, an arc connecting multiple facets, the arc representing a connection between information related to each of the multiple facets.

18. The computer-implemented method of claim 13, wherein the isolated brain wave components comprise at least one of:

an alpha brain wave component;
a beta brain wave component;
a theta brain wave component;
a delta brain wave component; or
a gamma brain wave component.

* * * * *

UNITED STATES PATENT AND TRADEMARK OFFICE
CERTIFICATE OF CORRECTION

| | | |
|---|---|---|
| PATENT NO. | : 11,963,783 B2 | Page 1 of 1 |
| APPLICATION NO. | : 17/411676 | |
| DATED | : April 23, 2024 | |
| INVENTOR(S) | : Dhiraj Jeyanandarajan | |

It is certified that error appears in the above-identified patent and that said Letters Patent is hereby corrected as shown below:

In the Claims

Column 17, Line 58 (Claim 6), change "isolated frequency" to --isolated--.

Column 20, Line 7 (Claim 16), change "brain wave component wave components" to --brain wave component--.

Signed and Sealed this
Second Day of July, 2024

Katherine Kelly Vidal
*Director of the United States Patent and Trademark Office*